US012779075B2

(12) United States Patent
Monsen

(10) Patent No.: US 12,779,075 B2
(45) Date of Patent: Nov. 3, 2026

(54) SCENT DELIVERY DEVICE AND METHOD OF MANUFACTURE THEREOF

(71) Applicant: Robert Anthony Monsen, Herriman, UT (US)

(72) Inventor: Robert Anthony Monsen, Herriman, UT (US)

( * ) Notice: Subject to any disclaimer, the term of this patent is extended or adjusted under 35 U.S.C. 154(b) by 285 days.

(21) Appl. No.: 18/765,144

(22) Filed: Jul. 5, 2024

(65) Prior Publication Data

US 2026/0007796 A1 Jan. 8, 2026

(51) Int. Cl.
*A61L 9/03* (2006.01)
*A61L 9/013* (2006.01)

(52) U.S. Cl.
CPC ................. *A61L 9/03* (2013.01); *A61L 9/013* (2013.01); *A61L 2209/131* (2013.01)

(58) Field of Classification Search
CPC . A61L 9/035; A61L 9/04; A61L 9/042; A61L 9/125; B01J 20/2805; B01J 20/28016; B01J 20/32; B01J 20/3202; B01J 20/3204
See application file for complete search history.

(56) References Cited

U.S. PATENT DOCUMENTS 4,293,602 A * 10/1981 Coffey ...................... A61L 9/01 428/905
5,246,919 A * 9/1993 King ......................... A61L 9/01 512/4
5,873,933 A * 2/1999 Mackey .................. C08L 1/284 106/205.1
7,521,413 B2 4/2009 Ochomogo et al.
7,632,348 B2 12/2009 Cowan et al.
7,820,188 B2 * 10/2010 Varanasi ............. A01M 1/2077 424/DIG. 8
8,157,873 B2 4/2012 Murphy et al.
8,409,822 B2 4/2013 Trevino et al.
8,652,221 B2 2/2014 Uptain et al.
9,066,501 B2 6/2015 Sia et al.
9,358,191 B2 6/2016 Hiramoto et al.
9,926,258 B2 3/2018 Kropf et al.
10,426,131 B2 * 10/2019 Quellet ................ A01K 1/0152
(Continued)

OTHER PUBLICATIONS

A. Card, "Estimating Soil Texture: Sandy, Loamy, or Clayey", Colorado State University, Dec. 2015 (Year: 2015).*
(Continued)

*Primary Examiner* — Jennifer Wecker
*Assistant Examiner* — Brady C Pilsbury
(74) *Attorney, Agent, or Firm* — Jason P. Webb; Pearson Butler

(57) ABSTRACT

There is a scent delivery device and method of manufacture thereof wherein a scent delivering granular media is disposed within an airtight or textile container. The granular media includes: free-flowing non-silica, non-garnet, and non-staurolite glacial remnant sand mixed in a drum with powdered orris root fixative physically bonded to the free-flowing non-silica non-garnet, and non-staurolite glacial remnant sand and a fragrance fixed to the orris root fixative. The airtight container is a clear glass jar with a lidded top in functional communication with a heating lamp such that heat from the lamp is directed to the container and thereby to the scent delivering granular media.

20 Claims, 3 Drawing Sheets

(56) References Cited

U.S. PATENT DOCUMENTS

| | | | |
|---|---|---|---|
| 10,808,366 | B2 | 10/2020 | Tetrault et al. |
| 10,980,908 | B1 * | 4/2021 | Brandenburg ............ A61L 9/12 |
| 2007/0117737 | A1 | 5/2007 | Artiga Gonzalez et al. |
| 2013/0202788 | A1 | 8/2013 | Mikkelsen et al. |
| 2017/0218263 | A1 | 8/2017 | Salla et al. |
| 2018/0369442 | A1 * | 12/2018 | Kelsen ............... G06K 7/10297 |
| 2019/0125915 | A1 * | 5/2019 | Roszell ................... A61L 9/014 |

OTHER PUBLICATIONS

Calcean, "Baha Play Sand", product web page published 2023 (Year: 2023).*

* cited by examiner

SCENT DELIVERY DEVICE AND METHOD OF MANUFACTURE THEREOF

BACKGROUND OF THE INVENTION

Field of the Invention

The present invention relates to scent delivery devices and methods of manufacture thereof, specifically to candle-style scent delivery devices.

Description of the Related Art

Scent delivery devices have a rich history dating back thousands of years, playing integral roles in religious rituals, cultural practices, home décor, and personal hygiene. Incense is perhaps the earliest device, which has been used since ancient times all over the world. Early incense was typically made from aromatic plant materials such as resins, herbs, and spices, and it is burned for its pleasant aroma as well as its perceived spiritual and purifying properties. Incense burners of different designs are used to contain and release the fragrant smoke, creating an immersive sensory experience.

Candles, another iconic scent delivery device, have a history that traces back to ancient civilizations such as those of the Egyptians and Romans. Initially, candles were primarily made from tallow (animal fat) or beeswax, and they served not only as a source of light but also as a means of dispersing pleasant fragrances. Throughout history, various techniques were developed to infuse candles with scents, such as blending fragrant oils into the wax or attaching aromatic materials to the wick. Candles are popular for both practical (e.g. lighting, scent masking/delivery) and decorative purposes.

Candles are often considered to be excellent scent delivery devices for several reasons. Firstly, they contain a combustible wick surrounded by wax, typically made from materials like paraffin, soy, or beeswax. This composition allows candles to burn slowly and evenly, gradually releasing their scent over an extended period. Secondly, candles have a large surface area exposed to the surrounding air, which facilitates the dispersal of fragrance molecules as the wax melts and evaporates. This enables the scent to fill a room relatively quickly and evenly. Additionally, candles provide a warm, flickering ambiance that enhances the sensory experience, making the fragrance delivery more immersive and enjoyable. Lastly, candles come in a wide variety of shapes, sizes, and styles, allowing for customization to suit different preferences and occasions, making them versatile and popular scent delivery devices. Candles have been criticized as allowing for exposure to dangerous chemicals such as but not limited to lead, formaldehyde, acetaldehyde, and acrolein. Further, a burning candle is a potential fire hazard and can leave soot residue and wax stains in the room in which it burns.

Additional devices include diffusers, sprays (e.g. perfumes/colognes, aerosol sprays), and potpourri. Diffusers work by dispersing essential oils or fragrance oils into the air through various methods such as evaporation (e.g. reed diffusors), heat, or ultrasonic vibrations. Ultrasonic diffusers break down the oils into fine mist particles, while heat-based diffusers use a gentle warmth to evaporate the oils, both releasing the fragrance into the surrounding space. Perfumes and colognes are generally used to deliver scent to a person and are spritzed on the skin. Aerosol sprays (which may include cleaning/deodorizing compositions) contain liquid fragrance formulations under pressure in a canister. When the nozzle is pressed, the pressure is released, propelling the fragrance into the air as a fine mist or spray, which quickly disperses and fills the room with the desired scent. Potpourri consists of dried flowers, herbs, and other aromatic materials that emit fragrance naturally. When placed in open containers or decorative bowls, potpourri releases its scent gradually into the air, particularly when stirred or exposed to airflow.

Orris root is known to be used as a scent fixative for potpourri and perfumery. In the context of potpourri, orris root serves multiple purposes. Firstly, its own natural fragrance adds a subtle, earthy aroma to the potpourri blend. Secondly, orris root acts as a fixative, helping to preserve the scents of other aromatic materials in the mixture. This prolongs the longevity of the potpourri's fragrance, allowing it to slowly release over time. To utilize orris root in potpourri, it is typically dried and powdered before being mixed with other dried flowers, herbs, and spices to create a fragrant blend. In perfumery, orris root is prized for its fixative properties. It helps to stabilize and extend the scent of other fragrant compounds in perfume formulations. Orris root is often processed to extract its essential oils or to produce orris butter, both of which are highly aromatic and contain compounds such as irones that bind to and retain fragrance molecules. Perfumers incorporate orris root extracts into their formulations to enhance the longevity and depth of the fragrance, ensuring that the scent evolves gracefully over time.

Some improvements have been made in the field. Examples of references related to the present invention are described below in their own words, and the supporting teachings of each reference are incorporated by reference herein:

U.S. Pat. No. 7,521,413, issued to Ochomogo et al., discloses cleaning composition with a limited number of natural ingredients contains alkyl polyglucoside, solvent and colloidal silica. The cleaning composition optionally has an additional amount of glycerol. The cleaning composition optionally has a small amount of fragrance. The cleaning composition can be used to clean hard surfaces and cleans as well or better than commercial compositions containing synthetically derived cleaning agents.

U.S. Pat. No. 9,926,258, issued to Kropf et al., discloses a formula (I) which act as photolabile pro-fragrances. The invention further relates to detergents or cleaning agents, cosmetic agents and air freshening products including ketones of said type. The invention also relates to a method for lastingly scenting surfaces and a method for lastingly fragrancing rooms using said ketones.

U.S. Pat. No. 9,358,191, issued to Hiramoto et al., discloses a deodorant composition containing, as the active component, a colored compound obtainable by reacting a polyphenol in a solvent showing alkalinity in the coexistence of an oxygen molecule at a reaction pH value of 6.5 or more. As a substitute for a polyphenol, use can be made of a plant extract containing a polyphenol but containing substantially no amino acid. It is also possible to further employ an amino acid. Furthermore, use can be made of a plant extract and/or a plant body containing a polyphenol and an amino acid.

U.S. Patent Application Publication No.: US20130202788A1, by Mikkelsen et al., discloses a non-aqueous self-standing rigid fragrance gel comprising fragrance oil and a hydroxylalkyl cellulose derivative. In the preferred embodiment of the present invention, about 4.0 weight percent or more of hydroxylpropyl cellulose converts fragrance oil into a rigid gel with pseudoplastic rheology. The pseudoplastic gel shears to allow coating of crystals and objects, with subsequent rigidity restored to at least 80%.

The inventions heretofore known suffer from a number of disadvantages which include releasing toxic chemicals into the air, being a fire hazard, staining surfaces, being difficult to clean, and not being kid or pet safe.

What is needed is a scent delivery device and/or method of manufacture thereof that solves one or more of the problems described herein and/or one or more problems that may come to the attention of one skilled in the art upon becoming familiar with this specification.

SUMMARY OF THE INVENTION

The present invention has been developed in response to the present state of the art, and in particular, in response to the problems and needs in the art that have not yet been fully solved by currently available scent delivery devices and methods of manufacture thereof. Accordingly, the present invention has been developed to provide a scent delivery device and method of manufacture thereof.

In one non-limiting embodiment, there is a scent delivery device, comprising one or more of: a container; a scent delivering granular media that may be disposed within the container, and/or may include including one or more of: free-flowing non-silica sand; orris root fixative that may be physically bonded to the free-flowing non-silica sand; and/or a fragrance that may be fixed to the orris root fixative.

It may be that the free-flowing non-silica sand is glacial remnant sand. It may be that the container is airtight and includes a removable opening. It may be that the container is a clear glass container. It may be that there is a heating lamp that may be functionally coupled to the container such that the heating lamp heats the container. It may be that the ratio of free-flowing non-silica sand to orris root fixative by volume is between about 10:1, 8:1, 6:1, 4:1, 2:1, and 1:1. It may be that the container is a textile bag. It may be that the free-flowing non-silica sand is also non-garnet sand and/or non-staurolite sand. It may be that the free-flowing non-silica sand has a grain size of less than about 0.5 mm, 0.25 mm, or 0.0625 mm.

In another non-limiting embodiment, there may be a method of manufacturing a scent delivery device, comprising the steps of one or more of: mixing free-flowing non-silica sand together with powdered orris root such that the powdered orris root physically bonds to the free-flowing non-silica sand while still retaining its free-flowing status thereby forming a quantity of free-flowing fixing medium; mixing a fragrance together with the free-flowing fixing medium such that the fragrance fixes thereto thereby generating a scent delivering granular media; and/or disposing a quantity of the scent delivering granular media within a container.

It may be that the steps of mixing are performed in a mixing drum. It may be that the step of mixing a fragrance is performed until the scent delivering granular media is darker in color than a color of free-flowing non-silica sand. It may be that the method does not include a step of curing the orris root and the fragrance. It may be that the ratio of free-flowing non-silica sand to powdered orris root by volume is between 10:1, 8:1, 6:1, 4:1, 2:1, and 1:1. It may be that the free-flowing non-silica sand is also non-garnet sand and non-staurolite sand. It may be that the free-flowing non-silica sand has a grain size of less than about 0.5 mm, 0.25 mm, or 0.0625 mm. It may be that the container is an airtight container. It may be that the airtight container is a lidded clear glass jar. It may be that the container is a textile bag.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims or may be learned by the practice of the invention as set forth hereinafter.

BRIEF DESCRIPTION OF THE DRAWINGS

In order for the advantages of the invention to be readily understood, a more particular description of the invention briefly described above will be rendered by reference to specific embodiments that are illustrated in the appended drawing(s). It is noted that the drawings of the invention are not to scale. The drawings are mere schematics representations, not intended to portray specific parameters of the invention. Understanding that these drawing(s) depict only typical embodiments of the invention and are not, therefore, to be considered to be limiting its scope, the invention will be described and explained with additional specificity and detail through the use of the accompanying drawing(s), in which.

DETAILED DESCRIPTION OF THE INVENTION

Figure 1:
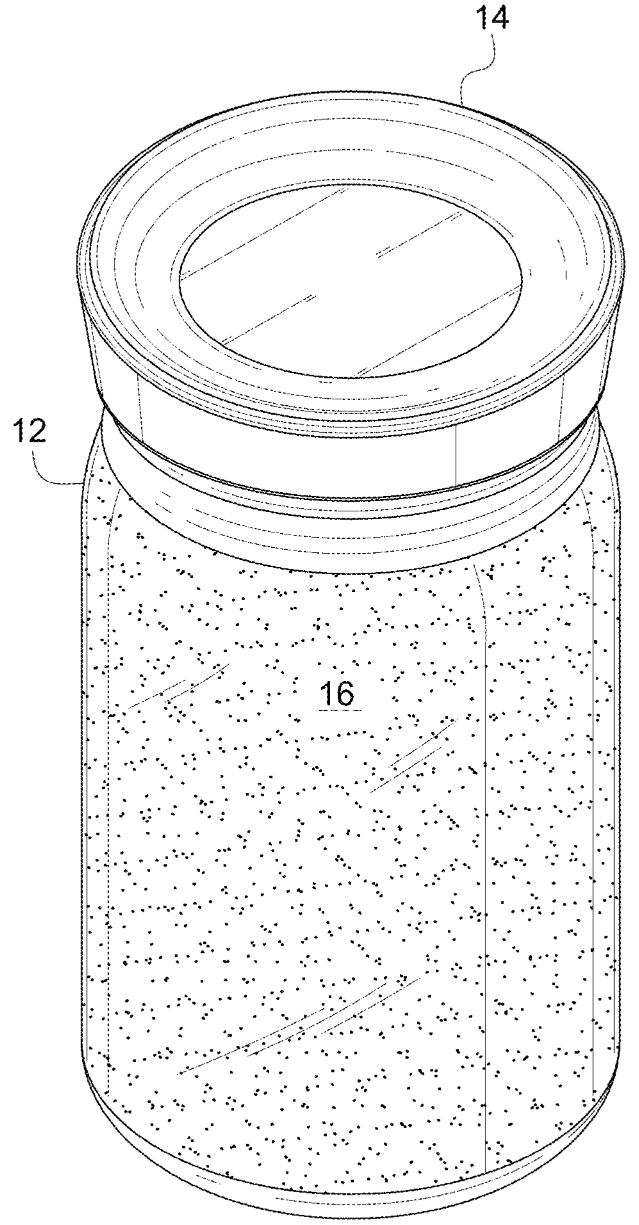
FIG. 1 is a perspective view of a scent delivery device according to one embodiment of the invention.

For the purposes of promoting an understanding of the principles of the invention, reference will now be made to the exemplary embodiments illustrated in the drawing(s), and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would occur to one skilled in the relevant art and having possession of this disclosure, are to be considered within the scope of the invention.

Reference throughout this specification to an "embodiment," an "example" or similar language means that a particular feature, structure, characteristic, or combinations thereof described in connection with the embodiment is included in at least one embodiment of the present invention. Thus, appearances of the phrases an "embodiment," an "example," and similar language throughout this specification may, but do not necessarily, all refer to the same embodiment, to different embodiments, or to one or more of the figures. Additionally, reference to the wording "embodiment," "example" or the like, for two or more features, elements, etc. does not mean that the features are necessarily related, dissimilar, the same, etc.

Each statement of an embodiment, or example, is to be considered independent of any other statement of an embodiment despite any use of similar or identical language characterizing each embodiment. Therefore, where one embodiment is identified as "another embodiment," the identified embodiment is independent of any other embodiments characterized by the language "another embodiment." The features, functions, and the like described herein are considered to be able to be combined in whole or in part one with another as the claims and/or art may direct, either directly or indirectly, implicitly or explicitly.

As used herein, "comprising," "including," "containing," "is," "are," "characterized by," and grammatical equivalents thereof are inclusive or open-ended terms that do not exclude additional unrecited elements or method steps. "Comprising" is to be interpreted as including the more restrictive terms "consisting of" and "consisting essentially of."

FIG. 1 is a perspective view of a scent delivery device according to one embodiment of the invention. There is shown a container with a lid including a quantity of scent delivery granular media. The illustrated scent delivery device conveniently delivers scent on demand in a manner similar to a candle, but without the soot, inconvenience, and hazard that lit candles bring.

The illustrated container 12 is airtight and includes a removable opening covered by the illustrated lid 14. It is a clear glass jar that is see-through, thereby allowing the user to see the granular media 16 disposed therein and protecting the contents from being spilled/lost/etc. While the illustrated container is of glass, it is understood that alternative embodiments of the invention may have containers of alternate materials, such as but not limited to ceramic, stone, wood, metal, paper, textile (e.g. a bag or sachet), and/or composite materials. In some embodiments, the container is not airtight (e.g. a textile sachet) and may not include a lid. Where the container is of a woven/textile material, the spacing between the weaves will generally be small enough such that the granular media does not escape through the spaces between the threads.

The illustrated lid 14 covers the removable opening of the container 12 and maintains the airtight seal when in place. When removed, the lid 14 allows for airflow to distribute the scent of the granular media 16 about the immediate vicinity. The lid may include one or more seals made of elastic materials (e.g. silicone, rubber) that acts as a gasket to maintain the airtight seal when the lid is in place.

The illustrated scent delivering granular media (granular media) 16 is disposed within the container. Advantageously, scent from the granular media is contained within the container until such time that the user wants to cause the scent to distribute within a space. The illustrated granular media includes free-flowing non-silica sand, an orris root fixative physically bonded to the free-flowing non-silica sand, and a fragrance fixed to the orris root fixative. Being free-flowing, the sand is able to conform to the shape of the container and is also easy to manage during manufacturing, storage, and distribution. Further, this allows the user to pour the sand, if desired, into a space or region which will increase the airflow and therefore increase the scent delivery.

In one non-limiting embodiment, the free-flowing non-silica sand is glacial remnant sand as opposed to river sand, volcanic sand, etc. Glacial remnant sand is a type of sediment that originates from the erosion and weathering of rocks by glaciers. As glaciers move, they grind down the underlying bedrock into fine particles. When the glaciers retreat, they leave behind these deposits, creating sand that often contains a mix of minerals, such as quartz and feldspar, and varying grain sizes. This sand can be found in regions that were once glaciated and is characterized by its well-rounded grains, indicative of the intense grinding process it underwent. Glacial remnant sand is often used in construction and landscaping due to its unique properties and historical significance.

It is believed that glacial remnant sand has characteristics that synergistically benefit the purposes of the final form of the scent delivering granular media. In particular, it is believed that glacial remnant sand has shape characteristics that prolong the usable life of the scent delivering granular media without unduly restricting the scent delivery by operation of packing structures that trap and allow airflow through the granular media at rates that are particularly conducive to scent delivery. This is because glacial remnant sand is more angular and less rounded than river sand but not as sharp-edged as volcanic sand. Accordingly, it packs in a manner different from either. Further, it is believed that the orris root powder physically bonds to the surface textures of glacial remnant sand in an improved manner, thus making manufacturing and use more efficient, reliable, and effective. In various non-limiting embodiments, the free-flowing non-silica sand has a grain size of less than about 0.5 mm, 0.25 mm, or 0.0625 mm.

The illustrated sand is non-silica sand, which advantageously reduces the abrasiveness of the granular media during manufacturing and use. It is generally understood in the that non-silica sand is sand that has a very low percentage of silica therein, generally less than 1% by weight. This reduces wear and tear on manufacturing equipment and also makes the end product less hazardous to the user (e.g. if children swallow the granular media). Non-silica glacial remnant sand, which typically refers to sand that is free from silica contamination or is low in silica content, can be sourced from specific geological deposits or regions where glacial processes have occurred without significant silica enrichment. Such may be sourced from: Northern Europe and Scandinavia: regions such as Finland, Sweden, and Norway have glaciated landscapes where sand deposits are relatively low in silica content compared to other regions; Northern North America: areas in northern Canada and parts of Alaska where glaciers have deposited sediments that yield glacial remnant sand with lower silica levels; and certain coastal regions: coastal areas influenced by glacial activity, such as parts of New Zealand, Iceland, or the Antarctic, have glacial sand deposits that are naturally low in silica.

In another non-limiting embodiment, the non-silica sand is also substantially free from garnet and staurolite (i.e. non-silica, non-garnet, and non-staurolite sand) to further reduce the abrasiveness of the granular media and/or to increase the effectiveness of the physical bonding with the orris root.

Orris root is a fragrant botanical ingredient derived from the rhizomes of the *Iris germanica, Iris florentina*, or *Iris pallida* plants. It is harvested, dried, and aged over several years to develop its distinctive violet-like aroma. Traditionally used in perfumery and as a fixative in potpourri and sachets, orris root imparts a warm, powdery scent that enhances and stabilizes other fragrances. In addition to its aromatic qualities, orris root has been employed in herbal medicine for its purported anti-inflammatory and digestive benefits. Its versatility extends to the culinary world, where it serves as a flavoring in gin and certain confectioneries.

Orris root powder is a finely ground edible substance made from the rhizomes of *Iris germanica, Iris florentina*, or *Iris pallida* plants. After harvesting, the rhizomes are dried and aged for several years to develop their signature violet-like fragrance, then milled into a fine powder. Renowned for its sweet, floral scent, orris root powder is a prized ingredient in perfumery, serving as a fixative to enhance and prolong the longevity of other fragrances. Beyond its use in perfumes, it is also utilized in potpourri, cosmetics, and as a natural flavoring agent in culinary applications, notably in gin and certain confectioneries. Additionally, orris root powder has historical applications in traditional medicine for its anti-inflammatory and digestive properties.

The illustrated granular media includes orris root powder physically bonded to the illustrated sand. Generally, sand is the primary ingredient, which makes sure that the granular media continues to exhibit physical properties that are more similar to sand than to orris root powder. Accordingly, there will generally be more sand by volume/weight than orris root. In various embodiments, it may be that the ratio of free-flowing non-silica sand to orris root fixative by volume is between about 10:1, 8:1, 6:1, 4:1, 2:1, and 1:1. In various embodiment, it may be that the ratio of free-flowing non-silica sand to orris root fixative by weight is between about 10:1, 8:1, 6:1, 4:1, 2:1, and 1:1.

The illustrated granular media 16 includes fragrance that is chemically bonded to the orris root. Fragrances are generally complex mixtures of aromatic compounds designed to produce a pleasant and distinctive scent. These compounds can be derived from natural sources, such as essential oils from plants and flowers, or synthesized in laboratories to create a wide array of scents. Fragrances play a crucial role in personal care products like perfumes, colognes, and body sprays, as well as in household items such as candles, air fresheners, and cleaning products. In some cases fragrances are fixed to orris root to prolong their utility (e.g. Chanel No. 19, Guerlain, Christian Dior Homme, and Prada Infusion d'Iris). In one non-limiting embodiment, the fragrance fixed to the orris root powder that is bonded to the sand is also bonded to orris root (e.g. before mixing the fragrance with the sand/root mixture), thereby further extending the life of the scent delivery device.

The following are non-limiting examples of fragrances:

Natural Essential Oils: Derived from plants and flowers through processes like steam distillation or cold pressing, these oils include lavender, rose, bergamot, and many others.

Synthetic Fragrance Oils: Created in laboratories to mimic natural scents or to develop entirely new fragrances, offering a wide range of possibilities in perfumery and other products.

Resins: Such as frankincense and myrrh, these aromatic substances are derived from tree sap and used in perfumes, incense, and spiritual practices.

Animal-Derived Fragrances: Historically sourced from animal secretions like musk (now largely replaced with synthetic alternatives) to impart a rich, warm scent to perfumes.

Fruits: Citrus fruits like lemon, orange, and grapefruit provide fresh, uplifting scents commonly used in perfumes and household products.

Flowers: Besides essential oils, flowers like jasmine, tuberose, and ylang-ylang contribute their unique floral fragrances to perfumes and cosmetics.

Herbs and Spices: Ingredients such as cinnamon, ginger, and peppermint provide aromatic compounds that are used in both fragrance and flavor applications.

Woods: Aromatic woods like sandalwood, cedarwood, and agarwood (oud) are prized for their deep, woody scents and are used in perfumes, incense, and aromatherapy.

Barks: For example, cinnamon bark and *cassia* bark are sources of fragrant oils used in perfumes and home fragrance products.

Seaweeds and Algae: Some marine plants contribute to fragrances used in skincare products and perfumes, offering unique oceanic and green notes.

According to one embodiment of the invention, there is a sand "candle" with no wax, no wick, and no flame. Such a device creates no black marks on the ceiling. It is kid and pet friendly and no more dangerous than leaving a light on (e.g. when used in conjunction with a heat lamp to increase scent distribution). It will not stain. If it is spilled it can be easily cleaned with a vacuum. It is warm to the touch when placed under a wax lamp configured to melt wax placed under it. It utilizes low abrasion sand (e.g. non-silica) which makes it safer for kids and less wear/tear on materials placed in contact with the sand (e.g. less likely to scratch the glass of a glass jar).

In another non-limiting embodiment, there is a sand "candle" with only three ingredients per scent (sand, orris root powder, and fragrance). There is a glass jar with a label with non-silica glacial remnant sand. There is a binder, which is orris root powder. There is a fragrance. The sand, and root powder are mixed in a mixing drum and then the fragrance is added. The final form is done mixing when the color changes (generally changing to be a little bit darker color, which indicates that the fragrance and orris root have bound to the sand).

Figure 2:
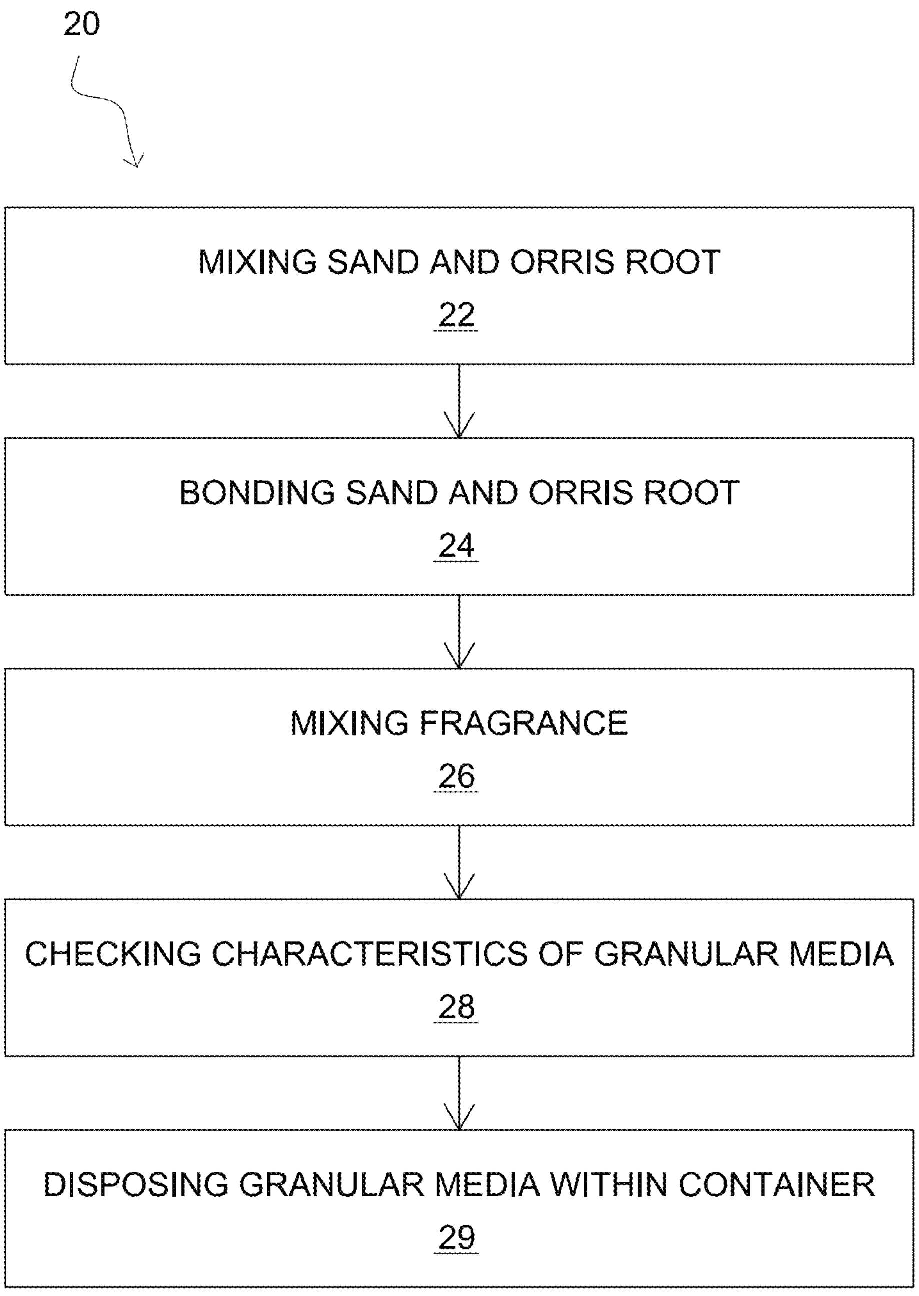
FIG. 2 is a flow chart showing a method of manufacturing a scent delivery device according to one embodiment of the invention.

FIG. 2 is a flow chart showing a method 20 of manufacturing a scent delivery device according to one embodiment of the invention. There is shown a step of mixing sand and orris root 22, then bonding sand and orris root 24, then mixing fragrance 26, then checking characteristics 28, then disposing granular media within a container 29. The illustrated method advantageously generates a sand "candle" that provides the benefits of a scent delivering candle without the danger, inconvenience, and mess of an actual burning candle.

The step of mixing sand and orris root allows for sand and orris root (generally powder) the bond with each other. Generally, one will provide more sand than orris root so that the resulting granular media retains free-flowing and visual properties of sand instead of being more like a caked powder with impurities. The substances may be scooped/shoveled or otherwise disposed within a mixing container, generally a mixing drum.

The step of bonding sand and orris root occurs as the materials are continually mixed together in a manner that distributes the orris root powder about the sand and is facilitated by physical impacts between the powder and sand, which occur in a mixing drum. Accordingly, while a certain amount a mixing may evenly distribute the materials amongst each other, that is the start of the bonding process, since the mixing must continue to allow for the orris root powder to adhere to the sand. As the bonding begins to occur, the material inside the drum begins to flow more like a single homogenous material that is sand-like, instead of seeming like a mixture of sand and fine powder. Once the mixture appears homogenous (free-flowing fixing medium), then one may proceed to the next step in the process.

The step of mixing fragrance includes disposing a quantity of fragrance together with the sand-like material of the bonded orris root and sand. This combination is then mixed so that the fragrance can chemically bond to the orris root powder. Orris root powder contains compounds such as irone and ionones, which act as fixatives. These molecules have a molecular structure that allows them to form stable complexes with other fragrance components. This bonding process helps to slow down the evaporation rate of the more volatile perfume ingredients, prolonging the overall scent duration. While it is common in the perfume industry to cure the chemical bond between the orris root powder and the fragrance, curing is generally not done on this process.

The step of checking characteristics generally includes making sure that there is no free powder or fragrance remaining in the final mixture (scent-delivering granular media). Further, s everything properly binds together, it has been observed that the final granular media is generally of a darker color than the original sand. Therefore, one of the checks is to see that this color change has occurred.

The step of disposing granular media within a container. This may be accomplished by simply pouring the free-flowing scent delivering granular media into a plurality of containers configured to receive the material, such as but not limited to glass jars and the like.

Figure 3:
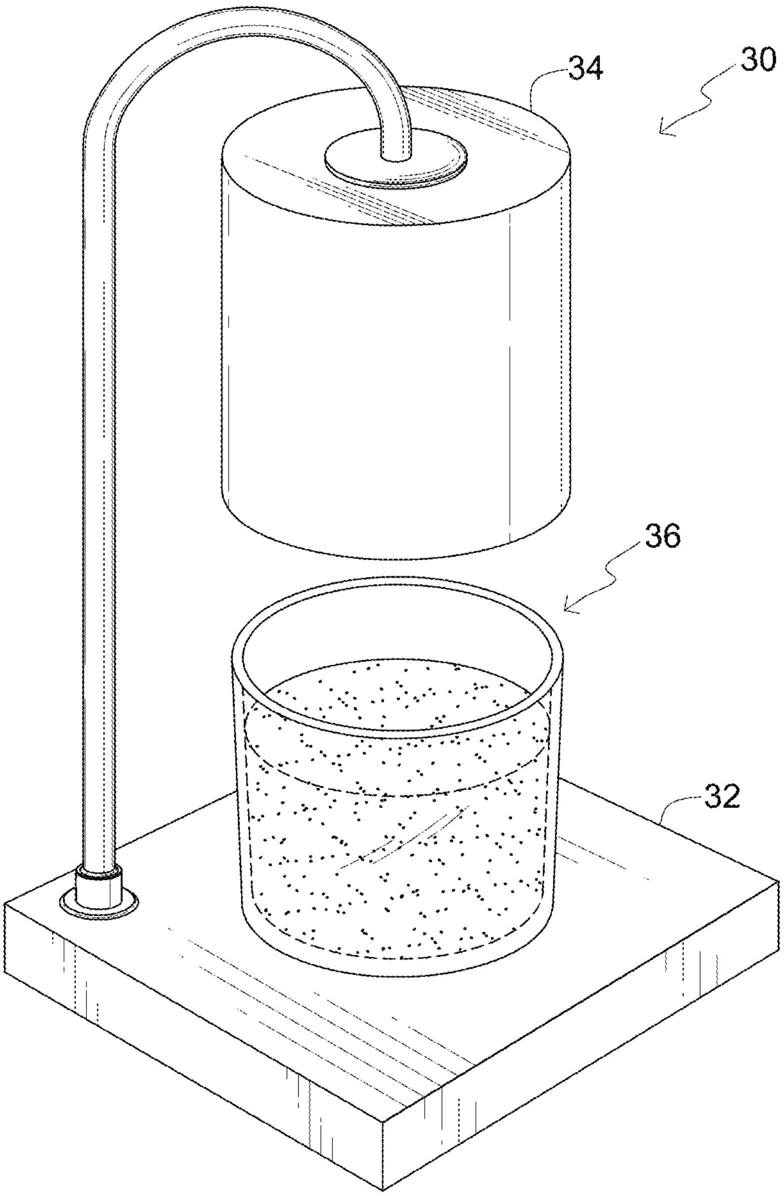
FIG. 3 is a perspective view of a scent delivery device according to one embodiment of the invention.

FIG. 3 is a perspective view of a scent delivery device according to one embodiment of the invention. There is shown a scent delivery device 30 including a heat base 32 having a lamp 34 shining on a container 36 resting on the base with scent delivering granular media disposed therein. Advantageously, this device provides effective and safe scent delivery to a space.

The illustrated base 32 and lamp 34 secure the container 36 in a location and position where the lamp can warm the scent delivering granular media, thus enhancing the distribution of scent included therein into the space where the lamp is present. Candle lamps, also known as candle lanterns or candle holders, are decorative and functional vessels designed to hold candles securely while protecting the flame from drafts and winds. Typically made from metal, glass, or other heat-resistant materials, candle lamps come in various styles and sizes, from traditional lanterns with clear or frosted glass panels to modern designs with intricate metalwork. They often feature handles or hooks for easy carrying or hanging and may include mechanisms for opening or closing to access the candle inside. The following are non-limiting examples of sources of candle lamps: Iittala Kivi Candle Holder by Iittala Group, PO Box 30, 00560 Helsinki, Finland; Yankee Candle Scenterpiece Easy Melt-Cup Warmer by The Yankee Candle Company, Inc., 16 Yankee Candle Way, South Deerfield, MA 01373, USA; and Vermont Lanterns Brass Miner's Candle Lantern Vermont Lanterns, 16 North Main Street, Suite 3, Randolph, VT 05060, USA.

It is understood that the above-described embodiments are only illustrative of the application of the principles of the present invention. The present invention may be embodied in other specific forms without departing from its spirit or essential characteristics. The described embodiment is to be considered in all respects only as illustrative and not restrictive. The scope of the invention is, therefore, indicated by the appended claims rather than by the foregoing description. All changes which come within the meaning and range of equivalency of the claims are to be embraced within their scope.

Thus, while the present invention has been fully described above with particularity and detail in connection with what is presently deemed to be the most practical and preferred embodiment of the invention, it will be apparent to those of ordinary skill in the art that numerous modifications, including, but not limited to, variations in size, materials, shape, form, function and manner of operation, assembly and use may be made, without departing from the principles and concepts of the invention as set forth in the claims. Further, it is contemplated that an embodiment may be limited to consist of or to consist essentially of one or more of the features, functions, structures, methods described herein.

What is claimed is:

1. A scent delivery device, comprising:
- a. a container; and
- b. a scent delivering granular media disposed within the container, including:
  - i. free-flowing non-silica sand;
  - ii. orris root fixative physically bonded to the free-flowing non-silica sand; and
  - iii. a fragrance fixed to the orris root fixative.

2. The scent delivery device of claim 1, wherein the free-flowing non-silica sand is glacial remnant sand.

3. The scent delivery device of claim 1, wherein the container is airtight and includes a removable opening.

4. The scent delivery device of claim 3, wherein the container is a clear glass container.

5. The scent delivery device of claim 4, further comprising a heating lamp functionally coupled to the container such that the heating lamp heats the container.

6. The scent delivery device of claim 1, wherein the ratio of free-flowing non-silica sand to orris root fixative by volume is between about 10:1, 8:1, 6:1, 4:1, 2:1, and 1:1.

7. The scent delivery device of claim 1, wherein the container is a textile bag.

8. The scent delivery device of claim 1, wherein the free-flowing non-silica sand is also non-garnet sand and non-staurolite sand.

9. The scent delivery device of claim 1, wherein the free-flowing non-silica sand has a grain size of less than about 0.5 mm, 0.25 mm, or 0.0625 mm.

10. A method of manufacturing a scent delivery device, comprising the steps of:
- a. mixing free-flowing non-silica sand together with powdered orris root such that the powdered orris root physically bonds to the free-flowing non-silica sand while still retaining its free-flowing status thereby forming a quantity of free-flowing fixing medium;
- b. mixing a fragrance together with the free-flowing fixing medium such that the fragrance fixes thereto thereby generating a scent delivering granular media; and
- c. disposing a quantity of the scent delivering granular media within a container.

11. The method of claim 10, wherein the steps of mixing are performed in a mixing drum.

12. The method of claim 10, wherein the step of mixing a fragrance is performed until the scent delivering granular media is darker in color than a color of free-flowing non-silica sand.

13. The method of claim 10, wherein the method does not include a step of curing the orris root and the fragrance.

14. The method of claim 10, wherein the ratio of free-flowing non-silica sand to powdered orris root by volume is between 10:1, 8:1, 6:1, 4:1, 2:1, and 1:1.

15. The method of claim 10, wherein the free-flowing non-silica sand is also non-garnet sand and non-staurolite sand.

16. The method of claim 10, wherein the free-flowing non-silica sand has a grain size of less than about 0.5 mm, 0.25 mm, or 0.0625 mm.

17. The method of claim 10, wherein the container is an airtight container.

18. The method of claim 17, wherein airtight container is a lidded clear glass jar.

19. The method of claim 10, wherein the container is a textile bag.

20. A scent delivery device, comprising:

a. a clear glass container having an open top;

b. a heating lamp functionally coupled to the container such that heat from the lamp is directed to the container; and c. a scent delivering granular media disposed within the container, including:

i. free-flowing non-silica, non-garnet, and non-staurolite glacial remnant sand;

ii. orris root fixative physically bonded to the free-flowing non-silica non-garnet, and non-staurolite glacial remnant sand; and iii. a fragrance fixed to the orris root fixative.

* * * * *